(12) United States Patent
Natali et al.

(10) Patent No.: US 9,360,437 B2
(45) Date of Patent: Jun. 7, 2016

(54) INSPECTION DEVICE AND METHOD FOR A SINGLE-DOSE CASING FOR A SUBSTANTIALLY TRANSPARENT CONTAINER FOR A SUBSTANTIALLY TRANSPARENT LIQUID

(75) Inventors: Luca Natali, Lugo (IT); Lorenzo Spagna, Guastalla (IT); Flavio Este, Selvazzano Dentro (IT)

(73) Assignee: SWISSLOG ITALIA S.P.A., Milan (MI) (IT)

( * ) Notice: Subject to any disclaimer, the term of this patent is extended or adjusted under 35 U.S.C. 154(b) by 137 days.

(21) Appl. No.: 14/113,450

(22) PCT Filed: May 29, 2012

(86) PCT No.: PCT/IB2012/052683
§ 371 (c)(1),
(2), (4) Date: Oct. 23, 2013

(87) PCT Pub. No.: WO2012/164489
PCT Pub. Date: Dec. 6, 2012

(65) Prior Publication Data
US 2014/0043604 A1 Feb. 13, 2014

(30) Foreign Application Priority Data

Jun. 1, 2011 (IT) ............................. BO2011A0319
Jun. 23, 2011 (IT) ............................. BO2011A0365

(51) Int. Cl.
*G01N 21/90* (2006.01)
*G06T 7/00* (2006.01)
*G01N 33/00* (2006.01)

(52) U.S. Cl.
CPC ............ *G01N 21/90* (2013.01); *G01N 21/9027* (2013.01); *G06T 7/001* (2013.01); *G01N 2033/0081* (2013.01); *G01N 2291/2695* (2013.01)

(58) Field of Classification Search
None
See application file for complete search history.

(56) References Cited

U.S. PATENT DOCUMENTS 2,479,743 A * 8/1949 Hall et al. ....................... 73/45.5
3,415,997 A * 12/1968 Vinzelberg et al. ............ 250/573
(Continued)

FOREIGN PATENT DOCUMENTS

DE 31 45 686 A1 5/1983
EP 0 042 336 A1 12/1981
(Continued)

OTHER PUBLICATIONS

Form PCT/ISA/220 Notification of Transmittal of International Search Report and Written Opinion of International Searching Authority issued in PCT/IB2012/052683, date of mailing Aug. 31, 2012 (1 page). Form PCT/ISA/210 International Search Report issued in PCT/IB2012/052683, date of mailing Aug. 31, 2012 (5 pages).
Form PCT/ISA/237 Written Opinion of the International Searching Authority issued in PCT/IB2012/052683, date of mailing Aug. 31, 2012 (9 pages).

(Continued)

*Primary Examiner* — Gordon J Stock, Jr.
(74) *Attorney, Agent, or Firm* — Flynn, Thiel, Boutell & Tanis, P.C.

(57) ABSTRACT

An inspection assembly for inspecting an at least partially transparent single-dose casing of the envelope type, in which there is arranged a substantially transparent container for containing a substantially transparent liquid. The assembly includes a substantially point-like light source and a diffusive screen. The container is provided between the light source and the diffusive screen, which is a side of the casing itself, in order to project onto the screen a profile of luminous intensity that is recorded.

11 Claims, 5 Drawing Sheets

(56) References Cited

U.S. PATENT DOCUMENTS

| | | | |
|---|---|---|---|
| 3,770,969 A * | 11/1973 | Ansevin et al. | 250/223 B |
| 3,900,266 A * | 8/1975 | Takahashi et al. | 356/442 |
| 4,028,553 A * | 6/1977 | Farcinade | 250/576 |
| 4,095,904 A * | 6/1978 | Klein et al. | 356/427 |
| 4,664,525 A * | 5/1987 | Tagaya | 356/428 |
| 4,843,231 A * | 6/1989 | Caloyannis et al. | 250/223 B |
| 5,280,170 A | 1/1994 | Baldwin | |
| 2006/0071002 A1 | 4/2006 | Hurst | |
| 2010/0246007 A1 | 9/2010 | Moon et al. | |

FOREIGN PATENT DOCUMENTS

| | | |
|---|---|---|
| EP | 1 126 273 A1 | 8/2001 |
| FR | 2997181 A1 * | 4/2014 |
| JP | 2003-202300 | 7/2003 |
| WO | WO 83/01835 | 5/1983 |
| WO | WO 2005/017814 A1 | 2/2005 |
| WO | WO 2007/045235 A1 | 4/2007 |
| WO | WO 2012/104681 A1 | 8/2012 |

OTHER PUBLICATIONS

Search Report of Italian Patent Office issued in BO2011A000365 with English translation of special categories of cited documents, Mar. 9, 2012 (3 pages).

Written Opinion of Italian Patent Office issued in BO2011A000365 with Supplemental Reasoned Statement in English, Jun. 23, 2011 (5 pages).

Form PCT/IPEA/416 Notification of Transmittal of International Preliminary Report on Patentability issued in PCT/IB2012/052683, Sep. 16, 2013 (1 page).

Form PCT/IPEA/409 International Preliminary Report on Patentability issued in PCT/IB2012/052683, Sep. 16, 2013 (9 pages).

Response dated May 7, 2013 responding to the Written Opinion of the International Searching Authority issued on Aug. 31, 2012 in Application No. PCT/IB2012/052683 (3 pages).

Response dated Jul. 11, 2013 responding to the second Written Opinion of the International Preliminary Examination Authority issued on Jun. 13, 2013 in Application No. PCT/IB2012/052683 (5 pages).

* cited by examiner

INSPECTION DEVICE AND METHOD FOR A SINGLE-DOSE CASING FOR A SUBSTANTIALLY TRANSPARENT CONTAINER FOR A SUBSTANTIALLY TRANSPARENT LIQUID

The present invention relates to an inspection assembly for a casing for a substantially transparent container containing a substantially transparent liquid.

In particular, it relates to an inspection assembly for a at least partially transparent casing of the envelope type, in which there is arranged a substantially transparent container for containing a substantially transparent liquid.

In the hospital sector, it is preferable for drugs, disinfectants, physiological solutions and other medical devices to be packaged separately in single doses for a more precise and regular distribution in the various divisions in accordance with the posology required by each patient. The arrival of systems for automatic control of the drugs in the hospital sector makes it necessary to provide for machines which individually package the tablets, compresses, phials or, more generally, the drug doses. Usually the doses are packaged in envelopes or wraps which are sealed, marked with a code identifying the contents and which must then be subjected to accurate checking in order to verify that each envelope is integral, contains one and only one dose, that the tablet or phial or the like is integral and that it is the correct one.

Patent Application No. PCT/IB2011/052053 by the same Applicant describes a device for packaging drugs in single-dose envelopes which provides, in addition to stations for filling envelopes, marking and sealing the envelopes, various stations for inspecting the envelopes, including a station for backlighting. In this station, a video camera is directed towards the envelope which contains the drug and which is illuminated by a source of diffused light which is positioned behind it. This solution allows display with optimum contrast of the edges of the opaque objects and therefore, in the case in question, the tablets, compresses, capsules, etc. The images thereby obtained can be automatically compared with the images expected for verifying the presence and the integrity of the drug contained in each envelope.

A problem of this inspection system of the known type is that it does not provide sufficient contrast in the event that the drug is a transparent liquid contained in a phial, small bottle, flask or other transparent container.

EP 1 126 273 describes a vision system to inspect a transparent plate-like object for flaws. It uses a point-like source to project a shadow of the object on a screen. If the plate-like object is slightly curved, it is preferably placed with the concavity towards the light source, to avoid distortions in the propagation of the light. Therefore, the system is not suitable for inspecting a filled phial, which is not a plate-like object and is typically highly curved.

WO 83/01835 discloses a device for the detection of impurities in a bottle; it has a plane light beam incising on a central portion of the bottle. The bottle is spun quickly and then stopped: the content continues to rotate and impurities cause a variation in the light transmitted by the bottle. It is an expensive and complex system not suitable to check wether the container is filled or not, since no variation of the light incurs in both cases. Moreover it is not suitable for phials sealed in a wrap or envelope.

An object of the present invention is to solve the problems of the prior art and in particular to provide an automatic inspection system which is also adapted to wraps containing phials, syringes, small bottles or another container which is substantially transparent and which contains a liquid (for example, a drug, a physiological solution, a disinfectant or another medical device) which is also substantially transparent. Another object is to provide a device which is economical, simple, reliable during use and secure.

In order to achieve the objects set out above, the present invention relates to an inspection device of the type indicated in the preamble of the present description, comprising a substantially point-like light source and a diffusive screen, the container being lens shaped and being provided between the light source and the diffusive screen in order to project onto the screen a profile of luminous intensity that is recorded by means for recording the luminous intensity. The term "transparent container" is intended to refer to a phial, small bottle, flask, syringe or other container which is substantially transparent for liquids which are substantially transparent, for example, drugs in the liquid state. The terms "phial" and "transparent container" are used below in a generally equivalent manner.

The invention further relates to an inspection method having the features set out in claim 8.

With a device according to the invention, the image acquired has optimum contrast and displays very clearly the edges of the phial. The phial, which interferes in a negligible manner with the propagation of diffused light, interferes substantially if the light projected thereon is directional because it acts substantially as a lens, in particular as a cylindrical lens in the case of phials or containers with a greater part of the body being cylindrical.

According to a particularly advantageous embodiment, the device further comprises a collimator means in order to collimate the light which is emitted by the substantially point-like light source, preferably a Fresnel lens. There is thereby obtained an approximately planar wave front which does not introduce distortions in the image recorded.

According to another advantageous embodiment, the envelope type casing comprises two adjoining films, between which the container is enclosed; the first film which is directed towards the substantially point-like light source is transparent and the second is diffusive and semi-transparent so as to define the diffusive screen in the envelope type casing.

Preferably, the inspection device provides for at least one deflecting mirror in order to position the substantially point-like light source and the recording means so as not to be in alignment with each other, in order to make the relative positioning thereof and positioning with respect to the position of the container more flexible and convenient.

The point-like light source is preferably an LED and the means for recording the luminous intensity preferably comprise a camera or a video camera.

The present invention is also directed towards equipment for packaging substantially transparent containers filled with a substantially transparent liquid in casings of the envelope type, according to claim 7, and toward a method to package and analyse substantially transparent containers filled with a substantially transparent liquid, according to claim 10.

Other features and advantages will be appreciated from the following detailed description of the operating principle and a preferred embodiment of the invention with reference to the appended drawings which are provided merely by way of non-limiting example and in which.

Figure 1:
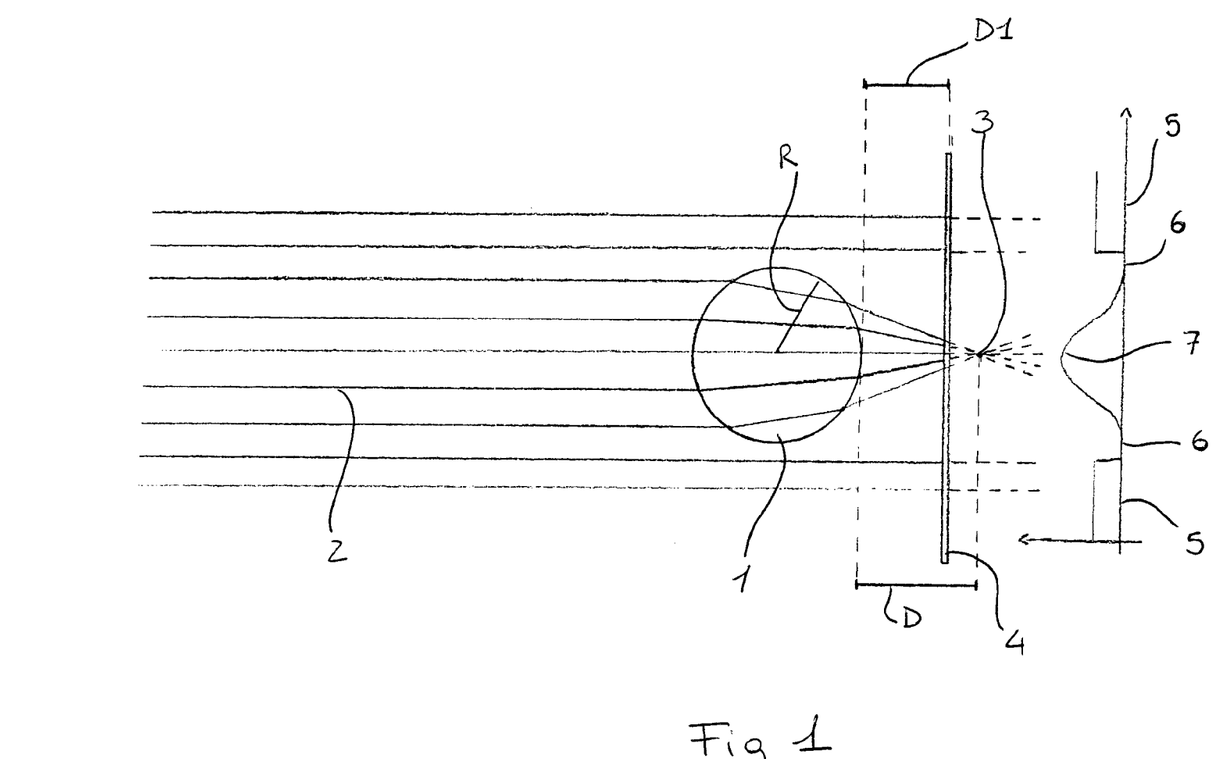
FIG. 1 illustrates the principle on which the present invention is based.

With reference to the drawings, FIG. 1 schematically illustrates the principle on which the present invention is based. The liquid contained in the phial 1 (in the image, it is viewed from above) has a refractive index n different from that of air, and therefore rays 2 which are incident substantially parallel with respect to the phial 1 are refracted at the air/phial and phial/air interface, generally being focused at a focal point 3. The focus 3 is positioned at a distance D from the phial 1 which depends on the refractive index n of the liquid and the radius R of the base of the phial in accordance with the relationship:

$$D = \frac{nR}{2(n-1)} - R,$$

or $$D = R\frac{2-n}{2(n-1)}.$$

If a screen 4 is positioned near the focus 3, the image projected onto the screen will have a profile of luminous intensity I with an extent similar to that illustrated in the drawing of FIG. 1. That drawing shows that the intensity I is constant in the zone 5 in which the rays have not intercepted the phial, has dark zones 6 in the region of the edges of the phial and has a peak 7 at the centre of the phial. That peak will become increasingly narrow and high as the screen is moved towards the focus. If it is moved away too far from the focus, the peak becomes wider and the dark zones become narrower until the dark zones disappear. Therefore, the screen is preferably held in the vicinity of the phial and, even more preferably, within a distance D1 of between 0 and two times D.

The refractive index of water is n=1.33, that of many oils, glass and many plastics materials is usually between 1.4 and 1.6. The refractive index of the liquid contained in the phial naturally varies in accordance with the type of liquid but, in the reasonable hypothesis that it is between 1.3 and 1.6, D will be approximately between 1.2 and 0.3 times the radius R of the phial and therefore the screen will preferably have to be positioned at a distance D1 between 0 and 2.4 times R.

In the drawing of FIG. 1 and the calculation of D and D1, the assumption has been made, naturally only by way of explanation, that the phial has a thickness of zero. Since the phial instead has a finite thickness, the propagation of the light is more complex, being a combination of propagation in glass and in liquid, but the fundamental concept remains the same. The assumption has further been made that the wave front of the incident beam is planar or that the rays are parallel. This is naturally an ideal case but images are also obtained with optimum contrast with rays which are not completely planar or even with a point-like source without a collimation lens, though the image is distorted. Finally, so that the light is focused by the container, it is necessary for the container and the liquid to be substantially transparent: though it is perfectly acceptable to have partial absorption of the incident light, it is important for the liquid and the container to have a negligible diffusivity so that the light passes through them without undergoing significant diffusion.

Experimentally, it has been found that the most convenient and effective solution is to position the screen in contact with the phial itself so that it is not necessary to move it in accordance with the dimensions of the phial or the liquid contained therein. Furthermore, it is thereby possible to acquire images with a good contrast even if the phial, small bottle or similar container does not have a circular base but instead has a base of any shape, for example, elliptical, but also square or more generally polygonal.

The sole requirement is that at least part of the collimated light beam is incident with respect to the walls of the container in a manner not perpendicular thereto. For example, in the case of a phial having a square base, it is sufficient that it is placed with its walls opportunely angled with respect to the beam's propagation direction or, more easily, that its edges are rounded. That requirement is naturally not problematic in the specific case of containers for medicines since they are not normally provided with sharp edges.

Figure 2:
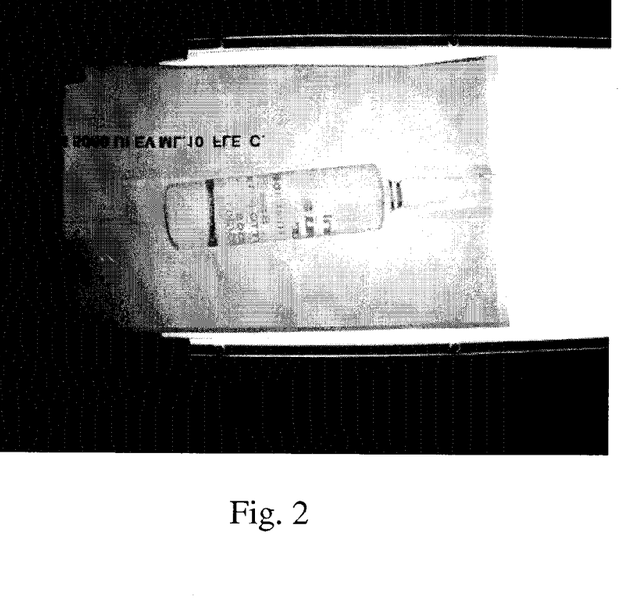
FIG. 2 shows an image which is obtained with an inspection device of known type and which is provided for comparison.
Figure 3:
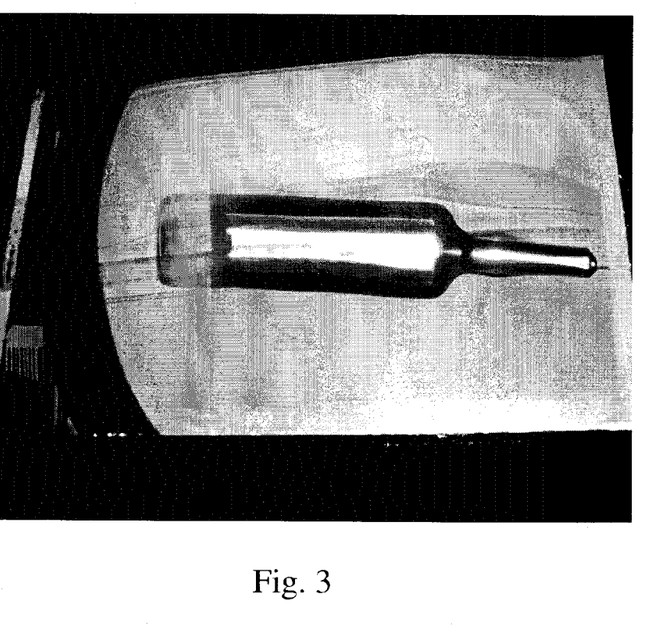
FIG. 3 shows an image obtained with an embodiment of the inspection device to which the present invention relates.

The positioning of the screen in contact with the container further allows images to be obtained with optimum contrast even if the container examined does not have the same cross-section over its entire height. For example, FIGS. 2 and 3 are images of a phial having the characteristic narrowing which are obtained with a known device having diffused backlighting and with the inspection device to which the present invention relates, respectively. In FIG. 2, the phial is visible to the naked eye but does not have sufficient contrast to be able to be automatically compared with a reference image. In FIG. 3, however, the edges are dark and have optimum contrast with respect to the clear background.

Figure 4:
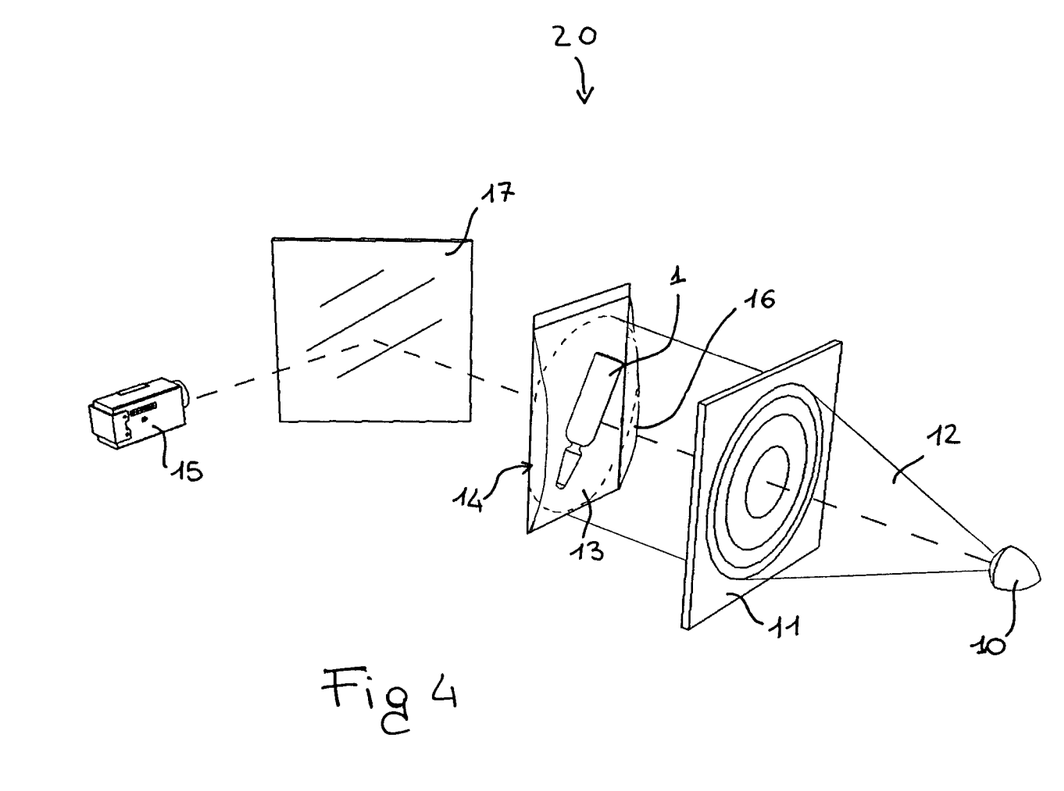
FIG. 4 is a schematic perspective view of a preferred embodiment of the invention.
Figure 5:
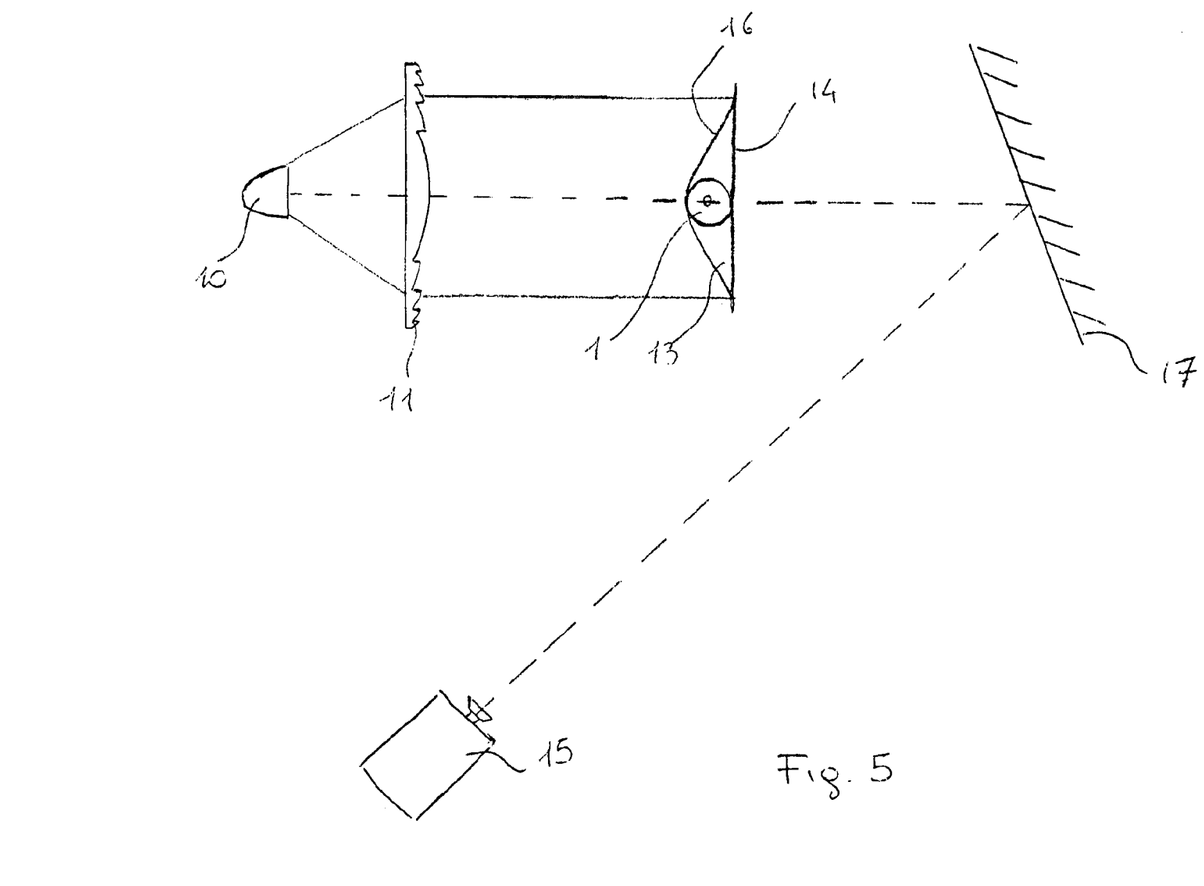
FIG. 5 is a view according to the arrow V of FIG. 4.

With reference to FIGS. 4 and 5, according to a preferred embodiment of the present invention, an inspection device 20 comprises a light source 10, for example an LED, which is coupled to a Fresnel lens 11 in order to produce a substantially collimated light beam 12 which is incident with respect to an envelope 13 which contains a phial 1 to be inspected. As evident from the drawings, the phial is placed with a main axis (the axis perpendicular to the base) substantially perpendicular to the beam's direction of propagation.

Naturally, there can be used lenses other than a Fresnel lens, provided that the focus is adapted to create a substantially collimated light beam with a substantially planar wave front. However, a Fresnel lens is preferable owing to its low cost and the compactness of the solution of resultant illumination.

Alternatively, for a less expensive device, it is possible to make use of a point-like light source, for example an LED, without any collimation lens. In this manner, the wave front which is incident with respect to the phial is not planar but instead substantially spherical. If, however, the source is positioned at a sufficient distance from the phial, images are obtained that are equally clear, though they may be distorted.

According to a particularly advantageous embodiment, the envelope or wrap 13 comprises a diffusive and semi-transparent side 14 which is constructed, for example, with a thin film of opaque plastics material, for example, orientated polypropylene, or paper, and a transparent side 16, for example, a film of transparent plastics material. In this manner, the transparent side 16 does not appreciably influence the propagation of the light, whilst the diffusive and semi-transparent side 14 acts as a screen. The profile of luminous intensity which is formed on that diffusive and semi-transparent side 14, is also visible at the rear face of the film, because it is constructed from a semi-transparent material. The profile is therefore recorded with a video camera 15. For convenience, one or more deflection mirrors 17 can be used so that the video camera 15 can be positioned outside the axis with respect to the incident beam, for example, at the same side as the light source.

Naturally, the video camera may be replaced by a photographic camera or any device for recording the light source.

The use of an envelope which itself acts as a screen prevents any problems linked to any inexact positioning of the screen with respect to the phial because it ensures that the screen and the phial are always in contact with each other. However, the use of a transparent envelope at both sides, in combination with a screen which is separate therefrom, should not be excluded. In this case, the screen may be semi-transparent in order to record the intensity profile behind it, or even non-transparent. In this second case, it will be advantageous to maintain the envelope at a sufficient distance from the screen because it is possible to record the intensity profile projected onto the face of the screen directed towards the envelope.

Figure 6:
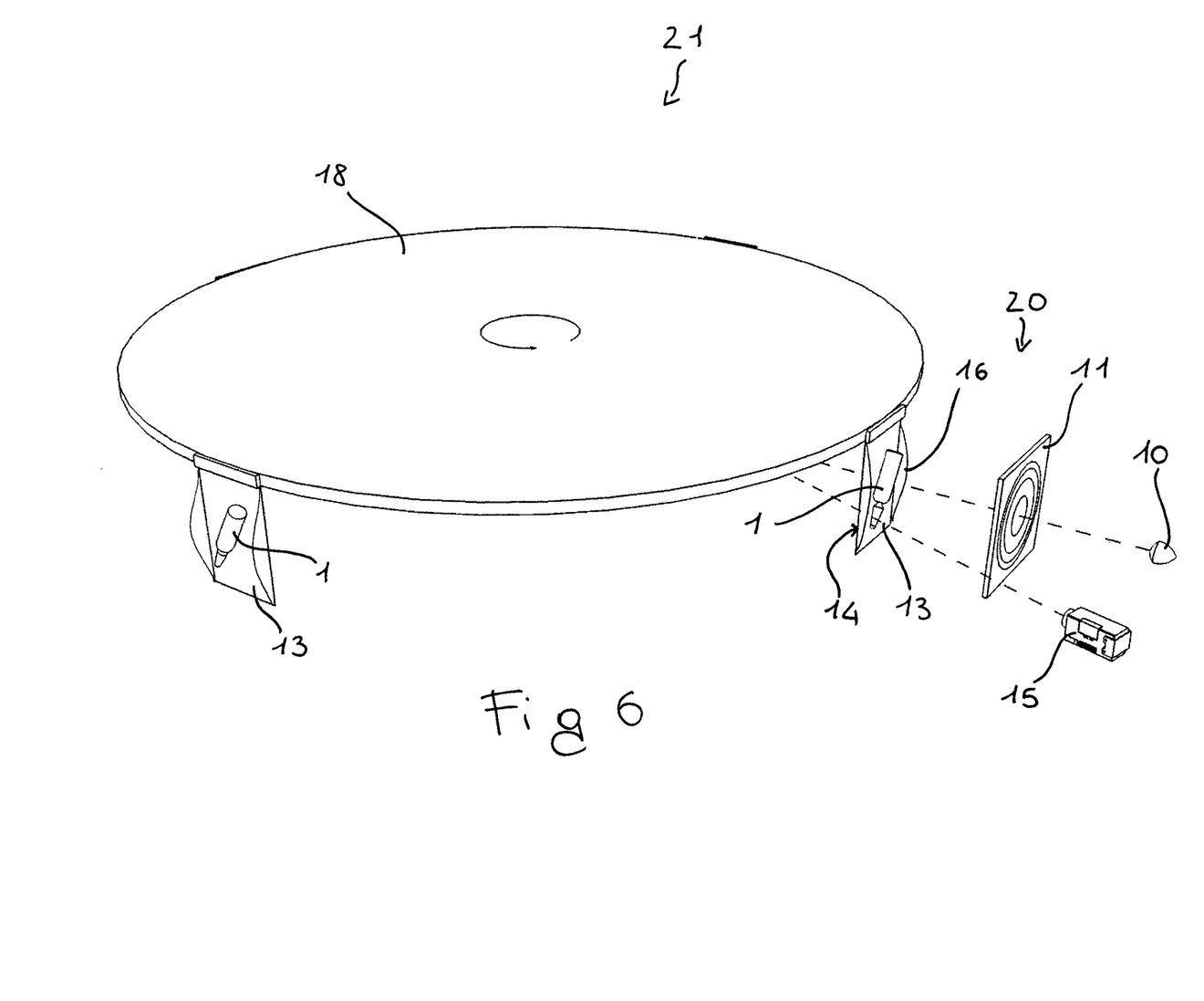
FIG. 6 is a schematic perspective view of equipment for the packaging comprising an inspection device according to the invention.

FIG. 6 illustrates a specific embodiment of the inspection device as a station integrated in a packaging device 21 of the same type as the one set out in the prior Patent Application No. PCT/IB2011/052053. The individual envelopes 13 are fixed on a rotating structure 18 with the transparent side 16 thereof directed towards the outer side of the rotating carriage, so that they are printed, filled and closed in a manner which is generally known and therefore not described in detail herein. One of the stations of the rotating structure is provided with a collimated light source (comprising a light source 10 and a lens 11) which frontally illuminates the envelope. Behind it (not visible in the drawings), there is positioned a deflecting mirror; a video camera 15 records the profile of light intensity projected onto the rear side (not visible) of the envelope and conveys the images to a processor for subsequent processing. This packaging device allows verification of the contents of the envelopes 13 after an identification of the contents has been printed thereon, and after the envelopes 13 have been sealed. In this manner, the verification of the contents by means of the device of the present invention also allows validation of the contents of the individual envelope 13 without it being possible to involve subsequent errors of identification of the contents, thereby increasing the general security and reliability of the automated control system for the drugs.

Such a device allows rapid acquisition of images of each envelope, comparison thereof with predefined reference images and establishment of whether the phial, small bottle or similar container received in the envelope is integral. It further allows verification of whether the phial is full or empty following, for example, a loss of liquid. A phial full of liquid demonstrates good optical properties for focusing, as described above. For that same reason, it is preferable, even though not absolutely necessary, for the phials to be externally packaged in such a manner that the most fragile part, i.e. the narrow portion, is full of liquid and therefore completely visible in order to verify the integrity thereof.

The assembly, the devices and the methods described above were developed for a single-dose pack, i.e. a pack containing a single phial, bottle or other container with an amount of a drug adequate for a single administration; envelops containing more than one phial or a series of single-dose envelops or packs connected to form a string should not be excluded.

Naturally, the principle of the invention remaining the same, the forms of embodiment and details of construction may be varied widely with respect to those described and illustrated, without thereby departing from the scope of the invention.

The invention claimed is:

1. An inspection assembly comprising an at least partially transparent single-dose envelope casing, in which there is arranged a substantially transparent container containing a substantially transparent liquid, the assembly comprising a substantially point-like light source and a diffusive screen, the container being lens shaped and being provided between the light source and the diffusive screen in order to project onto the screen a profile of luminous intensity that is recorded by means for recording the luminous intensity.

2. An inspection assembly according to claim 1, wherein the envelope casing comprises two adjoining films, between which the container is enclosed, a first of those films which is directed towards the substantially point-like light source being transparent, the second of those films being diffusive and semi-transparent in order to define the diffusive screen in the envelope casing.

3. An inspection assembly according to claim 1, further comprising a collimator means, placed between the substantially point-like light source and the casing in order to collimate light which is emitted by the substantially point-like light source.

4. An inspection assembly according to claim 1, wherein there is provision for at least one deflecting mirror in order to position the substantially point-like light source and the recording means so as not to be in alignment with each other.

5. An inspection assembly according to claim 1, wherein the substantially point-like light source is an LED.

6. An inspection assembly according to claim 1, wherein the recording means comprises a video camera.

7. Equipment for packaging and analysing substantially transparent containers containing a substantially transparent liquid, the equipment comprising a packaging station of said substantially transparent containers inside envelope casings, and an inspection assembly comprising an at least partially transparent single-dose envelope casing, in which there is arranged a substantially transparent container containing a substantially transparent liquid, the inspection assembly comprising a substantially point-like light source and a diffusive screen, the container being lens shaped and being provided between the light source and the diffusive screen in order to project onto the screen a profile of luminous intensity that is recorded by means for recording the luminous intensity.

8. An inspection method for an at least partially transparent envelope casing, in which there is arranged a substantially transparent container containing a substantially transparent liquid, comprising the steps of:
    providing a substantially point-like light source for emission of light, and a diffusive screen,
    providing the substantially transparent container between the substantially point-like light source and the diffusive screen in order to focus at least part of the light emitted by the light source and project same onto the diffusive screen a profile of luminous intensity,
    recording the profile of luminous intensity by means for recording the luminous intensity, and
    comparing the profile recorded with reference images to determine whether the container is integral and full.

9. A method according to claim 8, wherein the envelope casing comprises two adjoining films, between which the container is enclosed, a first of those films which is directed towards the substantially point-like light source being transparent, the second of those films being diffusive in order to define the diffusive screen in the envelope casing.

10. A method for packaging and inspecting a substantially transparent container, in which the substantially transparent container is packaged in an envelope casing and subsequently inspected by:

providing a substantially point-like light source for emission of light, and a diffusive screen, providing the substantially transparent container between the substantially point-like light source and the diffusive screen in order to focus at least part of the light emitted by the light source and project same onto the diffusive screen a profile of luminous intensity, recording the profile of luminous intensity by means for recording the luminous intensity, and comparing the profile recorded with reference images to determine whether the container is integral and full.

11. An inspection assembly comprising:

an envelope having a first side comprising a surface which is substantially transparent, the envelope sized to receive a single-dose container having liquid therein;

a single-dose container comprising a substantially transparent material and having a substantially transparent liquid therein, the container disposed in the envelope and comprising a curved lens-shaped surface;

a point-like light source capable of directing light in a light path direction toward the first side of the envelope and the container;

a diffusive screen disposed adjacent the container and downstream of the container in the light path direction; and an image recording device for recording an image from the diffusive screen.

\* \* \* \* \*